United States Patent [19]

Sakamoto et al.

[11] Patent Number: 5,157,155

[45] Date of Patent: Oct. 20, 1992

[54] BENZOYLUREA DERIVATIVE AND ITS PRODUCTION AND USE

[75] Inventors: Noriyaso Sakamoto, Takarazuka; Tatsuya Mori, Takarazuka; Tadashi Ohsumi, Nishinomiya; Toshihiko Yano, Ashiya; Izumi Fujimoto, Minoo, all of Japan; Yoji Takada, Versailles, France

[73] Assignee: Sumitomo Chemical Company, Limited, Osaka, Japan

[21] Appl. No.: 667,748

[22] Filed: Mar. 11, 1991

Related U.S. Application Data

[62] Division of Ser. No. 446,104, Dec. 5, 1989, abandoned, which is a division of Ser. No. 150,990, Feb. 1, 1988, Pat. No. 4,904,696.

[30] Foreign Application Priority Data

Feb. 4, 1987 [JP] Japan .................................. 62-23975

[51] Int. Cl.$^5$ .................. C07C 211/52; C07C 275/54; C07C 209/36; C07C 265/12
[52] U.S. Cl. .................................... 564/442; 560/338; 560/358; 564/44; 564/417
[58] Field of Search ......................................... 564/442

[56] References Cited

U.S. PATENT DOCUMENTS

| | | | |
|---|---|---|---|
| 2,446,519 | 8/1948 | Bean | 564/417 |
| 3,989,842 | 11/1976 | Wellinga et al. | 424/322 |
| 4,139,636 | 2/1979 | Sirrenberg et al. | 424/322 |
| 4,170,657 | 10/1979 | Rigterink | 424/322 |
| 4,457,943 | 7/1984 | Becher et al. | 424/322 |
| 4,625,062 | 11/1986 | Nagata et al. | 564/416 |
| 4,904,696 | 2/1990 | Sakamoto et al. | 564/44 |

FOREIGN PATENT DOCUMENTS

| | | |
|---|---|---|
| 702703 | 1/1964 | Canada . |
| 0071279 | 2/1983 | European Pat. Off. . |
| 0088343 | 9/1983 | European Pat. Off. . |
| 0154508 | 9/1985 | European Pat. Off. . |
| 0161019 | 11/1985 | European Pat. Off. . |
| 0226642 | 7/1987 | European Pat. Off. . |
| 0231152 | 8/1987 | European Pat. Off. . |
| 2726684 | 1/1979 | Fed. Rep. of Germany . |
| 3607298 | 9/1986 | Fed. Rep. of Germany . |
| 59-106454 | 6/1984 | Japan . |
| 61-277660 | 12/1986 | Japan . |
| 0536415 | 5/1941 | United Kingdom . |

OTHER PUBLICATIONS

C. R. Acad. Sc. Paris, T.258 (Jun. 22, 1964) Group 8. 6175–6177 Le Guyander et al, "Reduction Electrochimique etc.".

Veigand–Hilgetat, "Methods of Experiment in Organic Chemistry", Khimia Publishers, Moscow, 1958, p. 520.

Primary Examiner—Richard L. Raymond
Assistant Examiner—P. O'Sullivan
Attorney, Agent, or Firm—Stevens, Davis, Miller & Mosher

[57] ABSTRACT

The present invention relates to a novel benzoylurea derivative represented by the formula,

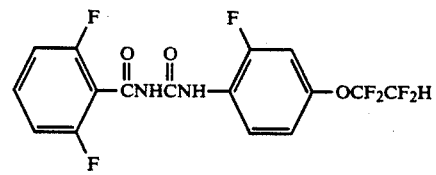

its production and insecticides containing it as an active ingredient.

The benzoylurea derivative is produced by reacting a benzamide compound represented by the formula,

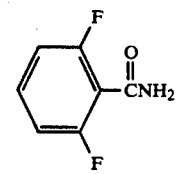

with an isocyanate compound represented by the formula,

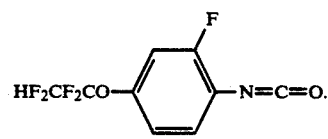

1 Claim, No Drawings

BENZOYLUREA DERIVATIVE AND ITS PRODUCTION AND USE

This is a division of application Ser. No. 446,104 filed Dec. 5, 1989, now abandoned, which in turn is a division of application Ser. No. 150,990, filed Feb. 1, 1988, now U.S. Pat. No. 4,904,696.

The present invention relates to a novel benzoylurea derivative represented by the formula (I),

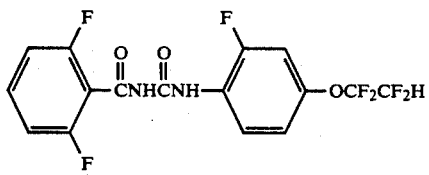

its production and insecticides containing it as an active ingredient.

The present inventors have made many studies to develop excellent insecticides, and as a result, have found that the benzoylurea derivative represented by the foregoing formula (I) (hereinafter referred to as present compound) has excellent insecticidal activity, particularly a very high insecticidal activity against the larvae or nymphs of insect pests, and also that it can be produced relatively cheaply. The present inventors thus attained to the present invention.

Hitherto, benzoylurea compounds belonging to a certain kind are known to have an insecticidal activity [U.S. Pat. Nos. 3,933,908, 4,139,636 and 4,457,943; E.P. No. 71279A1; Japanese Patent Publication Kokai (Laid-open) No. 106454/1984], and some of them are already on the market. Recently, however, it has been found that the present compound has an insecticidal activity superior to that of these compounds.

Specific examples of insect pests against which the present compound is particularly efficacious will be given below: Larvae of insect pests belonging to Lepidoptera such as diamond-back moth (*Plutella xylostella*), rice stem borer (*Chilo suppressalis*), armyworms and cutworms, Plusiid moths (Plusiinae), small white butterfly (*Pieris rapae crucivora*), casemaking clothes moth (*Tinea pellionella*), webbing clothes moth (*Tineola bisselliella*), etc.; larvae of insect pests belonging to Diptera such as house mosquitoes (Culex spp.) [e.g. *Culex pipiens pallens*], Anopheline mosquitoes (Anopheles spp.), Aedes mosquitoes (Aedes spp.), chironomid midges, houseflies (Muscidae), blow flies (Calliphoridae), flesh flies (Sarcophagidae), tabanid flies (Tabanidae), black flies, etc.; nymphs of insect pests belonging to Dictyoptera such as German cockroach (*Blattella germanica*), smokybrown cockroach (*Periplaneta fuliginosa*), brown cockroach (*Periplaneta brunnea*), American cockroach (*Periplaneta americana*), etc.; and larvae of other insect pests belonging to Coleoptera or Hymenoptera.

Also, the present compound is low in toxicity to warm-blooded animals so that it can be orally administered by mixing with feeds for animals, to domestic animals such as cattle, pigs, horses, sheep, goats, chickens, etc. As a result, the present compound is excreted from animals as undecomposed, so that the larvae of insect pests living in the excrement of domestic animals [e.g. housefly, false stablefly (*Muscina stabulans*), little housefly (*Fannia canicularis*), blow flies (Calliphoridae), flesh flies (Sarcophagidae), sepsid flies (Sepsidae)], can be exterminated.

The present compound represented by the formula (I) can be produced by the following methods.

METHOD A

A method of reacting a benzoylisocyanate compound represented by the formula (II),

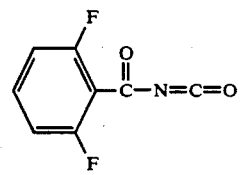

with an aniline compound represented by the formula (III),

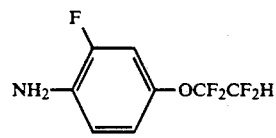

METHOD B

A method of reacting a benzamide compound represented by the formula (IV),

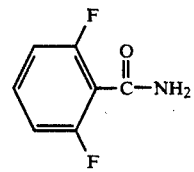

with an isocyanate compound represented by the formula (V),

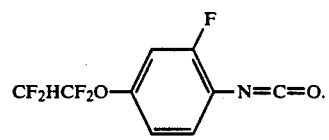

In the foregoing Methods A and B, the reaction is usually carried out in the presence of an inert solvent. The solvent usable includes for example aromatic hydrocarbons (e.g. benzene, toluene, xylene), halogenated hydrocarbons (e.g. chlorobenzene, carbon tetrachloride, chloroform, methylene chloride, 1,2-dichloroethane), ethers (e.g. diethyl ether, tetrahydrofuran, dioxane), ketones (e.g. acetone, methyl ethyl ketone, methyl isobutyl ketone), dimethyl sulfoxide, dimethylformamide, nitromethane and mixtures thereof.

In Methods A and B, the reaction can generally be carried out under normal pressure, and usually for a period of 1 to 50 hours. The amounts of the starting compounds are generally in an equimolar ratio, but one of the starting compounds may be used in excess.

In Methods A and B, the reaction temperature is not particularly limited, but it is in a range of generally from 0° to 80° C., usually from room temperature (ca. 25° C.) to 60° C. for Method A, and generally from room temperature to 160° C., usually from 80° to 130° C. for Method B.

The present compound thus obtained can be purified if necessary by means such as column chromatography, recrystallization, etc.

In the production of the present invention, the aniline compound represented by the formula (III), a starting compound is a novel compound, and it can be produced, for example, by the methods described below:

SYNTHETIC METHOD 1

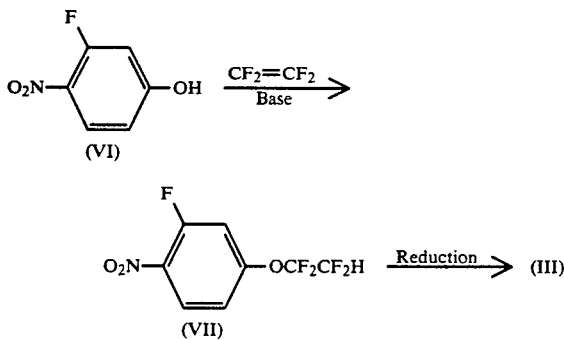

SYNTHETIC METHOD 2

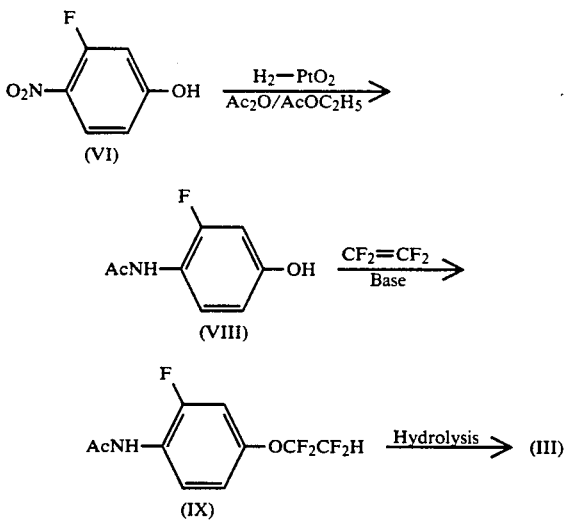

SYNTHETIC METHOD 3

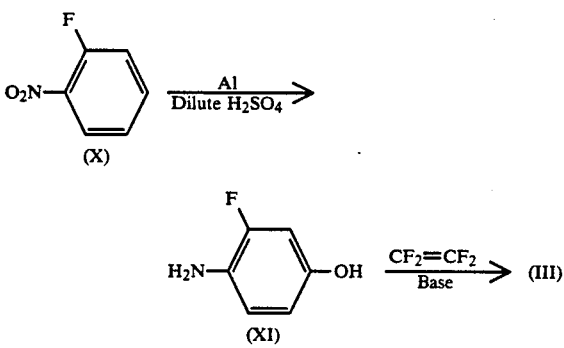

In Synthetic method 1, the aniline compound (III) is obtained by reacting 3-fluoro-4-nitrophenol (VI) with tetrafluoroethylene in the presence of a base and reducing the resulting compound (VII), for example, with iron in the presence of an acid or catalytically reducing the compound (VII) with hydrogen in the presence of platinum dioxide.

In Synthetic method 2, the aniline compound (III) is obtained by catalytically reducing 3-fluoro-4-nitrophenol (VI) with hydrogen in the presence of acetic anhydride, ethyl acetate and platinum dioxide, reacting the resulting compound (VIII) with tetrafluoroethylene in the presence of a base to obtain a compound (IX) and hydrolyzing the acetylamino group of the compound (IX) by the usual method.

In Synthetic method 3, the aniline compound (III) is obtained by reacting cheap and easily available o-fluoronitrobenzene with metallic aluminum in the presence of a dilute sulfuric acid to obtain 3-fluoro-4-aminophenol (XI) in a high yield, and reacting the compound (XI) with tetrafluoroethylene in the presence of a basic catalyst.

This reaction is usually carried out under the following condition. Metallic aluminum used to produce the aminophenol (XI) may have any form of a powder and a chip, but a powder is preferably used. The concentration of the sulfuric acid is from 1 to 50%, preferably about 10%, and the reaction temperature is from 50° to 100° C., preferably from 90° to 95° C.

In carrying out this reaction, the amount of sulfuric acid used is from 1 to 5 times by mole, preferably about 3 times by mole based on 1 mole of o-fluoronitrobenzene. The amount of metallic aluminum is from 1 to 3 times by mole, preferably about 1.7 times by mole based on the same.

The basic catalyst used in reacting the aminophenol (XI) with tetrafluoroethylene includes for example caustic alkalis (e.g. caustic potash), alkali carbonates (e.g. potassium carbonate), etc., but caustic potash is preferably used.

The reaction is usually carried out in an inert solvent, and the solvent includes for example dimethylformamide, mixed solvents of dimethylformamide and other inert solvents (e.g. toluene, acetonitrile, dioxane), etc., but dimethylformamide is preferably used. The reaction temperature is from 30° to 150° C., preferably from 70° to 100° C.

In carrying out this reaction, the amount of tetrafluoroethylene used is not less than an equimolar amount based on 1 mole of the aminophenol (XI). The reaction product thus obtained can easily be purified if necessary by distillation, etc.

Said aniline compound (III) can be converted to an isocyanate compound represented by the formula (V) by reacting it with phosgene according to the usual method, and usually, this reaction is carried out under the following condition. The amount of phosgene used in this reaction is usually from 1 to 5 times by mole based on 1 mole of the aniline compound (III). In this reaction, an inert solvent is usually used, and normally, it includes for example hydrocarbons (e.g. hexane, heptane, benzene, toluene), halogenated hydrocarbons (e.g. dichloromethane, chloroform, 1,2-dichloroethane, chlorobenzene) and mixtures of two or more of them. This reaction well proceeds at a temperature ranging from room temperature to the boiling point of the solvent. The reaction product thus obtained can easily be purified if necessary by distillation, etc.

When the present compound is used as an active ingredient for insecticides, it may be used as it is without adding any other ingredients. Usually, however, it is formulated into emulsifiable concentrates, wettable powders, dusts, granules, oil sprays, aerosols, poisonous baits, etc. by mixing with solid carriers, liquid carriers, gaseous carriers, surface active agents, other auxiliaries for formulation, baits, etc.

In these preparations, the content of the present compound, which is an active ingredient, is from 0.01 to 95% by weight. The solid carrier includes for example fine powders or granules of kaolin clay, attapulgite clay, bentonite, terra abla, pyrophyllite, talc, diatomaceous earth, calcite, corn stalk powder, walnut shell powder, urea, ammonium sulfate, synthetic hydrated silicon dioxide and the like. The liquid carrier includes for example aliphatic hydrocarbons (e.g. kerosene), aromatic hydrocarbons (e.g. benzene, toluene, xylene, methylnaphthalene), halogenated hydrocarbons (e.g. dichloromethane, trichloroethane, carbon tetrachloride), alcohols (e.g. methanol, ethanol, isopropanol, ethylene glycol, cellosolve), ketones (e.g. acetone, methyl ethyl ketone, cyclohexanone, isophorone), ethers (e.g. diethyl ether, dioxane, tetrahydrofuran), esters (e.g. ethyl acetate), nitriles (e.g. acetonitrile, isobutyronitrile), acid amides (e.g. dimethylformamide, dimethylacetamide), dimethyl sulfoxide, vegetable oils (e.g. soybean oil, cotton seed oil) and the like. The gaseous carrier includes for example freon gas, LPG (liquefied petroleum gas), dimethyl ether and the like. The surface active agent used for emulsification, dispersion, wetting, etc. includes for example anionic surface active agents such as the salt of alkyl sulfates, alkyl(aryl)sulfonates, dialkyl sulfosuccinates, the salt of polyoxyethylene alkylaryl ether phosphoric acid esters, naphthalenesulfonic acid/-formalin condensates, etc., and nonionic surface active agents such as polyoxyethylene alkyl ether, polyoxyethylene polyoxypropylene block copolymers, sorbitan fatty acid esters, polyoxyethylene sorbitan fatty acid esters, etc. The auxiliary for formulation such as fixing agents, dispersing agents, etc. includes for example lignosulfonates, alginates, polyvinyl alcohol, gum arabic, molasses, casein, gelatin, CMC (carboxymethyl cellulose), pine oil, agar, etc. The stabilizer includes for example alkyl phosphates [e.g. PAP (isopropyl acid phosphate), TCP (tricresyl phosphate)], vegetable oils, epoxidized oils, the foregoing surface active agents, antioxidants (e.g. BHT, BHA), fatty acid salts (e.g. sodium oleate, calcium stearate), fatty acid esters (e.g. methyl oleate, methyl stearate) and the like.

These preparations thus obtained may be used as they are or diluted with water. Also, they may be used in mixture with other insecticides, acaricides, nematocides, fungicides, herbicides, plant growth regulators, fertilizers, soil improvers, feeds for animals, etc.

When the present compound is used as insecticides, its dosage rate is usually from 0.5 to 500 g per 10 ares, and its application concentration is from 1 to 1000 ppm when emulsifiable concentrates, wettable powders, etc. are used by diluting with water. Dusts, granules, oil sprays, aerosols, etc. are used as they are without dilution.

The present compound will be illustrated in more detail with reference to the following production examples, formulation examples and test examples, but the present invention is not limited to these examples.

PRODUCTION EXAMPLE 1

0.15 Gram of 2-fluoro-4-(1,1,2,2-tetrafluoroethoxy)aniline was dissolved in 5 ml of toluene, and to the resulting solution was added dropwise a solution of 0.12 g of 2,6-difluorobenzoylisocyanate in 3 ml of toluene with stirring and ice-cooling. After completion of the addition, the reaction solution was stirred overnight at room temperature, and 5 ml of n-hexane was added. The precipitated crystals were filtered off and dried to obtain 0.19 g of N-2,6-difluorobenzoyl-N'-[2-fluoro-4-(1,1,2,2-tetrafluoroethoxy)phenyl]urea as white crystals.
Yield: 70%
m.p.: 173°-174° C.

PRODUCTION EXAMPLE 2

0.16 Gram of 2,6-difluorobenzamide, 0.25 g of 2-fluoro-4-(1,1,2,2-tetrafluoroethoxy)phenylisocyanate and 20 ml of xylene were added to a reactor and stirred under reflux for 24 hours. The reaction solution was cooled and concentrated to obtain a crude product. This crude product was subjected to chromatography on silica gel to obtain 0.24 g of N-2,6-difluorobenzoyl-N'-[2-fluoro-4-(1,1,2,2-tetrafluoroethoxy)phenyl]urea as white crystals.
Yield: 60%
m.p.: 172°-173° C.

PRODUCTION EXAMPLE 3

After dissolving 1.15 g of 3-fluoro-4-nitrophenol in 10 ml of dioxane, the resulting solution was violently stirred at about 60° C. for 15 minutes under the stream of a tetrafluoroethylene gas in large excess of said phenol. After quickly adding 0.04 g of potassium hydroxide, the solution was violently stirred for 2 hours under the same condition. The reaction solution was cooled, and after adding water, extracted with two 100-ml portions of diethyl ether. The ether layers were combined, dried and concentrated to obtain a yellow oily product as a residue. This oily product was subjected to chromatography on silica gel to obtain 0.20 g of 2-fluoro-4-(1,1,2,2-tetrafluoroethoxy)nitrobenzene.
Yield: 10.6%
$^{19}$F-NMR (CDCl$_3$/CF$_3$COOH): $\delta$ (ppm) $-10$(2F, s), $-33$(1F, s), $-57$(2F, d, $J_{F-H}=54$ Hz)

0.20 Gram of 2-fluoro-4-(1,1,2,2-tetrafluoroethoxy)nitrobenzene, 0.03 g of platinum dioxide and 5 ml of ethyl acetate were added to a reactor, and the atmosphere in the reactor was replaced by a hydrogen stream with stirring. Stirring was then continued at room temperature for 2 hours while introducing a hydrogen gas. Thereafter, the reaction solution was filtered off, and the filtrate was concentrated to obtain 0.15 g of 2-fluoro-4-(1,1,2,2-tetrafluoethoxy)aniline.
Yield: 85%
$n_D^{25.5}$: 1.446
$^{19}$F-NMR (CDCl$_3$/CF$_3$COOH): $\delta$ (ppm) $-10.5$(2F, s), $-52.5$(1F, s), $-57.5$(2F, d, $J_{F-H}=53$ Hz)

PRODUCTION EXAMPLE 4

5.0 Grams of 3-fluoro-4-nitrophenol, 3.57 g of acetic anhydride, 0.72 g of platinum dioxide and 50 ml of ethyl acetate were added to a reactor, and the atmosphere in the reactor was replaced by a hydrogen stream with stirring. Stirring was then continued at room temperature for 6 hours while introducing a hydrogen gas. Thereafter, the reaction solution was filtered off, and the filtrate was washed with two 50-ml portions of a 5% aqueous sodium hydrogencarbonate solution, dried and concentrated. The residue was subjected to chromatography on silica gel to obtain 4.47 g of 4-acetylamino-3-fluorophenol.

Yield: 83% m.p.: 124° C.

0.93 Gram of 4-acetylamino-3-fluorophenol, 0.15 g of potassium carbonate and 15 ml of dimethylformamide were added to a reactor and stirred for 20 minutes at an oil bath temperature of from 60° to 70° C. Thereafter, this solution was violently stirred at the same temperature for 1 hour under the stream of a tetrafluoroethylene gas in excess of said phenol. The reaction solution was cooled and after adding water, extracted with two 100-ml portions of diethyl ether. The ether layers were combined, washed with water, dried and concentrated to obtain a crude product. This crude product was subjected to chromatography on silica gel to obtain 1.46 g of 4-acetylamino-3-fluoro-1-(1,1,2,2-tetrafluoroethoxy)benzene.

Yield: 98%

$^{19}$F-NMR (CDCl$_3$/CF$_3$COOH): δ (ppm) −10(2F, s), −47(1F, s), −57(2F, d, $J_{F-H}$=53 Hz)

0.60 Gram of 4-acetylamino-3-fluoro-1-(1,1,2,2-tetrafluoroethoxy)benzene and 10 ml of a 20% aqueous hydrochloric acid were added to a reactor and stirred under reflux for 2 hours. After cooling the reaction solution, a 5% aqueous sodium hydrogencarbonate solution was added to make the solution weakly alkaline. The reaction solution was then extracted with two 100-ml portions of diethyl ether. The ether layers were combined, dried and concentrated to obtain a yellow oily product as a residue. This oily product was subjected to chromatography on silica gel to obtain 0.40 g of 2-fluoro-4-(1,1,2,2-tetrafluoroethoxy)aniline.

Yield: 81%

PRODUCTION EXAMPLE 5

2.03 Grams of o-fluoronitrobenzene, 0.70 g of aluminum powder, 43 ml of water and 4.4 g of conc. sulfuric acid were added to a reactor and stirred at an inner temperature of from 90° to 95° C. for 40 minutes. After cooling the reaction solution, a 5% aqueous sodium hydrogencarbonate solution was added to make the reaction solution weakly alkaline. The reaction solution was then extracted with three 100-ml portions of diethyl ether. The ether layers were combined, dried and concentrated to obtain a crude product. This crude product was subjected to chromatography on silica gel to obtain 1.58 g of 3-fluoro-4-aminophenol.

Yield: 86% m.p.: 137°–138° C.

0.70 Gram of 3-fluoro-4-aminophenol, 0.06 g of potassium hydroxide and 10 ml of dimethylformamide were added to a reactor and stirred for 20 minutes at an oil bath temperature of from 60° to 70° C. This solution was then violently stirred at the same temperature for 2 hours under the stream of a tetrafluoroethylene gas in excess of said phenol. The reaction solution was cooled and after adding water, extracted with two 150-ml portions of diethyl ether. The ether layers were combined, washed with water, dried and concentrated to obtain a crude product. This crude product was subjected to chromatography on silica gel to obtain 1.00 g of 2-fluoro-4-(1,1,2,2-tetrafluoroethoxy)aniline.

Yield: 80%

Formulation examples will be shown. Parts in the examples are by weight.

FORMULATION EXAMPLE 1

Ten parts of the present compound, 14 parts of polyoxyethylene styrylphenyl ether, 6 parts of calcium dodecylbenzenesulfonate, 35 parts of xylene and 35 parts of dimethylformamide are well mixed to obtain an emulsifiable concentrate.

FORMULATION EXAMPLE 2

Twenty parts of the present compound, 10 parts of fenitrothion, 3 parts of calcium lignosulfonate, 2 parts of sodium lauryl sulfate and 65 parts of synthetic hydrated silicon dioxide are well pulverized and mixed to obtain a wettable powder.

FORMULATION EXAMPLE 3

One part of the present compound, 2 parts of carbaryl, 87 parts of kaolin clay and 10 parts of talc are well pulverized and mixed to obtain a dust.

FORMULATION EXAMPLE 4

Five parts of the present compound, 1 part of synthetic hydrated silicon dioxide, 2 parts of calcium lignosulfonate, 30 parts of bentonite and 62 parts of kaolin clay are well pulverized and mixed. The resulting mixture is well kneaded with water, granulated and dried to obtain a granule.

Test examples will be shown. Compounds used as a control are shown by compound symbols in Table 1.

TABLE 1

| Compound symbol | Structural formula | Remark |
| --- | --- | --- |
| (A) | 2,6-difluorophenyl–CNHCNH–(4-chlorophenyl) with two C=O groups | Diflubenzuron (compound described in U.S. Pat. No. 3,933,908). |
| (B) | 2-chlorophenyl–CNHCNH–(4-OCF$_3$-phenyl) with two C=O groups | Triflumuron (compound described in U.S. Pat. No. 4,139,636). |

TABLE 1-continued

| Compound symbol | Structural formula | Remark |
|---|---|---|
| (C) | (2,6-difluorobenzoyl)-(2,5-dichloro-3,4-difluorophenyl) diurea | Teflubenzuron (compound described in U.S. Pat. No. 4,457,943). |
| (D) | (2,6-difluorobenzoyl)-(3,5-dichloro-4-OCF₂CHF₂-phenyl) diurea | Compound No. 1 described in E.P. No. 71279A1. |
| (E) | (2,6-difluorobenzoyl)-(3-chloro-4-OCF₂CF₂H-phenyl) diurea | Compound unknown to the literatures. m.p. 158.7° C. |
| (F) | (2,6-difluorocyclohexylcarbonyl)-(3-chloro-4-OCF₂CHFCl-phenyl) diurea | Compound No. 18 described in U.S. Pat. No. 4,139,636. |
| (G) | (2,6-difluorobenzoyl)-(3-chloro-4-OCF₃-phenyl) diurea | Compound No. 29 described in U.S. Pat. No. 4,139,636. |
| (H) | (2,6-difluorobenzoyl)-(2-fluoro-4-chlorophenyl) diurea | Compound No. 1 described in Japanese Patent Publication Kokai (Laid-open No. 106454/1984. |
| (I) | $CH_3S$, $CH_3$ C=N—OCNHCH₃ | Methomyl |

TEST EXAMPLE 1

The emulsifiable concentrate of the present compound prepared according to Formulation example 1 was diluted with water so that the active ingredient concentration was 3.5 ppm. Thereafter, 100 ml of the aqueous dilute solution thus obtained was put in a 180-ml polyethylene cup, and 20 last instar larvae of common mosquito (*Culex pipiens pallens*) were liberated therein. The larvae were bred on a bait until emergence to obtain an emergence inhibitory ratio (two replications).

The results are shown in Table 2.

TABLE 2

| Test compound | Emergence inhibitory ratio (%) |
|---|---|
| Present compound | 100 |
| No treatment | 10 |

TEST EXAMPLE 2

Two milliliters each of the 200,000-fold aqueous dilute solutions (corresponding to 0.5 ppm) of emulsifiable concentrates prepared from the present compound and controls according to Formulation example 1 was applied onto 13 g of artificial diet for tobacco cutworm (*Spodoptera litura*), and the diet was put in a polyethylene cup of 11 cm in diameter. Then, ten fourth instar larvae of tobacco cutworm were liberated in the cup.

After six days, the dead and alive were examined to obtain mortality (two replications).

The results are shown in Table 3.

TABLE 3

| Test compound | Mortality (%) |
| --- | --- |
| Present compound | 100 |
| (A) | 5 |
| (B) | 0 |
| (C) | 20 |
| (D) | 5 |
| (E) | 5 |
| (F) | 20 |
| (G) | 30 |
| (H) | 10 |
| (I) | 0 |
| No treatment | 5 |

TEST EXAMPLE 3

One milliliter each of the 67,000-fold aqueous dilute solutions (corresponding to 1.5 ppm) of emulsifiable concentrates prepared from the present compound and controls according to Formulation example 1 was applied onto 5 g of artificial diet for rice stem borer (*Chilo suppressalis*) which had been previously prepared in a polyethylene cup of 5.5 cm in diameter. Then, ten 10-day old larvae of rice stem borer were liberated in the cup. After eight days, the dead and alive were examined to obtain mortality (two replications).

The results are shown in Table 4.

TABLE 4

| Test compound | Mortality (%) |
| --- | --- |
| Present compound | 100 |
| (A) | 30 |
| (B) | 5 |
| (C) | 45 |
| (D) | 40 |
| (E) | 10 |
| (F) | 15 |
| (G) | 0 |
| (H) | 35 |
| (I) | 5 |
| No treatment | 5 |

What is claimed is:

1. An aniline compound represented by the formula,

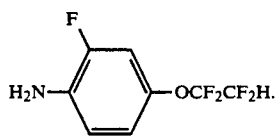

* * * * *